US006330062B1

(12) United States Patent
Corn et al.

(10) Patent No.: US 6,330,062 B1
(45) Date of Patent: Dec. 11, 2001

(54) FOURIER TRANSFORM SURFACE PLASMON RESONANCE ADSORPTION SENSOR INSTRUMENT

(75) Inventors: Robert M. Corn; Michael J. Green; Stephen C. Weibel, all of Madison, WI (US); Tony G. Frutos, Santa Ana, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/303,260

(22) Filed: Apr. 30, 1999

(51) Int. Cl.[7] ..................................................... G01N 21/55
(52) U.S. Cl. .......................................... 356/445; 356/451
(58) Field of Search ................................ 356/453, 128, 356/445, 451; 250/339.01–339.15

(56) References Cited

U.S. PATENT DOCUMENTS

| 4,997,278 | 3/1991 | Finlan et al. | 356/128 |
| 5,955,729 | * 9/1999 | Nelson et al. | 250/282 |

OTHER PUBLICATIONS

*Analytical Chemistry News & Features*, vol. 70,13, "SPR of Ultrathin Organic Films," report, by Anthony G. Frutos et al., pp. 449A through 455A.

"Surface Plasmon Resonance Introduction" report, pp. 1–5; "Fiber SPR Sensors" report, pp. 1–4; and "Biosensing with SPR" report, pp. 1–4, from Virginia Tech website, Apr. 12, 1999.

* cited by examiner

*Primary Examiner*—Robert H. Kim
*Assistant Examiner*—Phil Natividad
(74) *Attorney, Agent, or Firm*—Emrich & Dithmar

(57) ABSTRACT

Adsorption of molecules onto a thin metallic surface such as of gold, silver or copper is measured by surface plasmon resonance (SPR) using Fourier Transform (FT) spectroscopy. Reflectance spectra from a prism/metallic film sample surface at a fixed angle of incidence is measured with FT spectroscopy. The reflectance spectrum exhibits a pronounced minimum due to the SPR effect, which can be shifted by changing the angle of incidence or metallic film thickness. The position of the reflectance minimum shifts in wavelength with the adsorption of molecules onto the gold surface due to a change in the index of refraction at the interface. The FT-SPR sensor instrument provides wavelength stability and reproducibility of the resonance wavelength to permit detection of small wavelength shifts, and also substantially increases the spectral range over which the SPR measurements can be made. A beam of broadband radiation from a Michelson interferometer is directed through an SPR sample cell and onto a detector where the output signal is processed using standard FT techniques.

13 Claims, 6 Drawing Sheets

FOURIER TRANSFORM SURFACE PLASMON RESONANCE ADSORPTION SENSOR INSTRUMENT

This invention was made with United States government support awarded by the following agencies:

NSF Grant No.:9626607

The United States has certain rights in the invention.

FIELD OF THE INVENTION

This invention relates generally to the study of thin films as well as surface and interface effects and is particularly directed to a Fourier Transform surface plasmon resonance approach which is particularly adapted for studying ultrathin layer phenomenon such as the adsorption of a thin layer of molecules onto the surface of a chemically modified thin metal film.

BACKGROUND OF THE INVENTION

Surface plasmon resonance (SPR) is used in the nondestructive study of surfaces, interfaces, and very thin layers, and has recently been found to be particularly adapted for the study of immunologic phenomenon such as antigen-antibody reactions and antigen stimulation of tissue. A surface plasmon is an oscillation of free electrons propagated along the surface of a conductor which is typically in the form of a thin metal film of gold, silver or copper. Transverse-magnetic (TM) polarized energy in an evanescent field excites surface plasmons on the thin metal film. The characteristics of the resonance are directly related to the refractive indices of materials on both sides of the metal film. By including the sample to be measured as a layer on one side of the metal film, changes in the refractive index of the sample can be monitored by measuring changes in the evanescent field to surface plasmon coupling efficiency. Surface plasmons represent the quanta of oscillations of surface charges produced by application of an external electric field to a conducting medium.

The surface selectivity of SPR arises from the enhancement of the optical electric fields at metal surfaces when surface plasmon polaritons (SPPs) are created at the metal/dielectric surface. SPPs are coupled photon-plasmon surface electromagnetic waves that propagate parallel to the metal/dielectric interface. The intensity of the optical electric fields associated with an SPP decays exponentially in distance away from the metal surface, with a typical decay length for an SPP into the dielectric being on the order or 200 nm. SPPs cannot be created on an isolated planar metal surface, but rather require a prism or grating coupling geometry for exciting SPPs. Thus, surface plasmon resonance is achieved by using the evanescent wave which is generated when a p-polarized light beam is totally internally reflected at the boundary of a medium having a high dielectric constant, such as glass. The free electron oscillation is affected by the refractive index of the material adjacent the metal surface which forms the basis of SPR measurements.

In a typical SPR scanning angle experiment, p-polarized light from a laser is directed through a prism onto a metal film on which is disposed a thin sample layer being studied. The prism-sample assembly is mounted to a rotation stage, which allows scanning of the incident angle of the laser beam. As the angle of incidence of the laser beam is varied, surface plasmon resonance is evidenced as a sharp dip in the intensity of the laser beam internally reflected within the prism at a particular angle of incidence. The angle of incidence at which resonance occurs is affected by the refractive index of the thin sample layer disposed on the metal film. The angle of incidence corresponding to resonance is thus a direct measure of the characteristics of the thin sample layer. In the case of immunoassays, the measured angle of incidence corresponding to resonance represents a direct measure of the state of reaction between an antibody and its antigen. This SPR method is limited to use over a narrow angular range, limiting the index of refraction measurement range. In addition, lack of precision in the angular control will affect the reproducibility of the SPR measurement results.

Another SPR technique involves the coupling of a laser source to the sample prism in a focused beam and detecting the reflected light with a charge coupled device (CCD) detector. Other methods take advantage of the wavelength dependence of the SPR. Instead of scanning the angle, these methods scan the wavelength by dispersing reflected light into its constituent wavelengths with a light-dispersing prism or grating, and detecting the resonance with a CCD or linear array detector. Yet another technique makes use of a tunable-diode laser to scan the wavelength over the resonance wavelength region.

The present invention addresses the limitations of and improves upon the prior art by coupling a Fourier transform spectrometer to surface plasmon resonance measurements for the study of thin films as well as surface and interface phenomena. Fourier transform spectrometers are widely used for the analysis of adsorption and reflection characteristics of materials. These spectrometers provide intensity modulated light to sampling media with the use of various types of interferometers. These interferometric spectrometers provide fast data acquisition rates, high signal-to-noise outputs, high wavelength precision and reproducibility, and high ordinate precision. In addition, the wavelength region of operation of these spectrometers has a wide range and can be optimized by appropriate selection of light sources, beamsplitter materials, and detectors. The aforementioned characteristics provide improved measurement capability for SPR over prior surface plasmon resonance measurement approaches.

OBJECTS AND SUMMARY OF THE INVENTION

Accordingly, it is an object of the present invention to study adsorption onto chemically modified metal surfaces from the gas phase as well as from liquid solutions.

It is another object of the present invention to provide for the non-destructive study of surface and interface phenomenon as well as the characteristics and properties of very thin layers.

Yet another object of the present invention is to monitor the adsorption of biological molecules such as DNA, proteins, antibodies or enzymes from aqueous solutions either in situ or ex situ.

A further object of the present invention is to measure the surface plasmon resonance effect on a very thin surface film as a function of wavelength using Fourier Transform spectroscopy.

A still further object of the present invention is to provide for the optical measurement and analysis of immunologic phenomenon such antigen-antibody reactions or antigen stimulation of tissue.

This invention contemplates apparatus for monitoring the adsorption of molecules onto a thin metal film, the apparatus comprising a source of an interferometrically modulated broadband beam of electromagnetic radiation; a beam processing arrangement for collimating and polarizing the beam of electromagnetic radiation; a prism transparent to electromagnetic radiation and having first and second surfaces, wherein a first surface of the thin metal film is in intimate contact with the second surface of the prism, and wherein the beam of electromagnetic radiation is incident upon the first surface of the prism and is internally reflected by the prism at its second surface; an arrangement for introducing the molecules to a second, opposed surface of the thin metal film so as to form molecular attachment thereon, wherein the beam of electromagnetic radiation gives rise to surface plasmon resonance at the metal film/molecular attachment interface having characteristics dependent upon the adsorption of molecules on the thin metal film; and a detector responsive to the internally reflected beam of electromagnetic radiation for providing an output signal representing the surface plasmon resonance on the thin metal film, wherein the output signal is processed using Fourier Transform techniques.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF PREFERRED EMBODIMENTS

Figure 1:
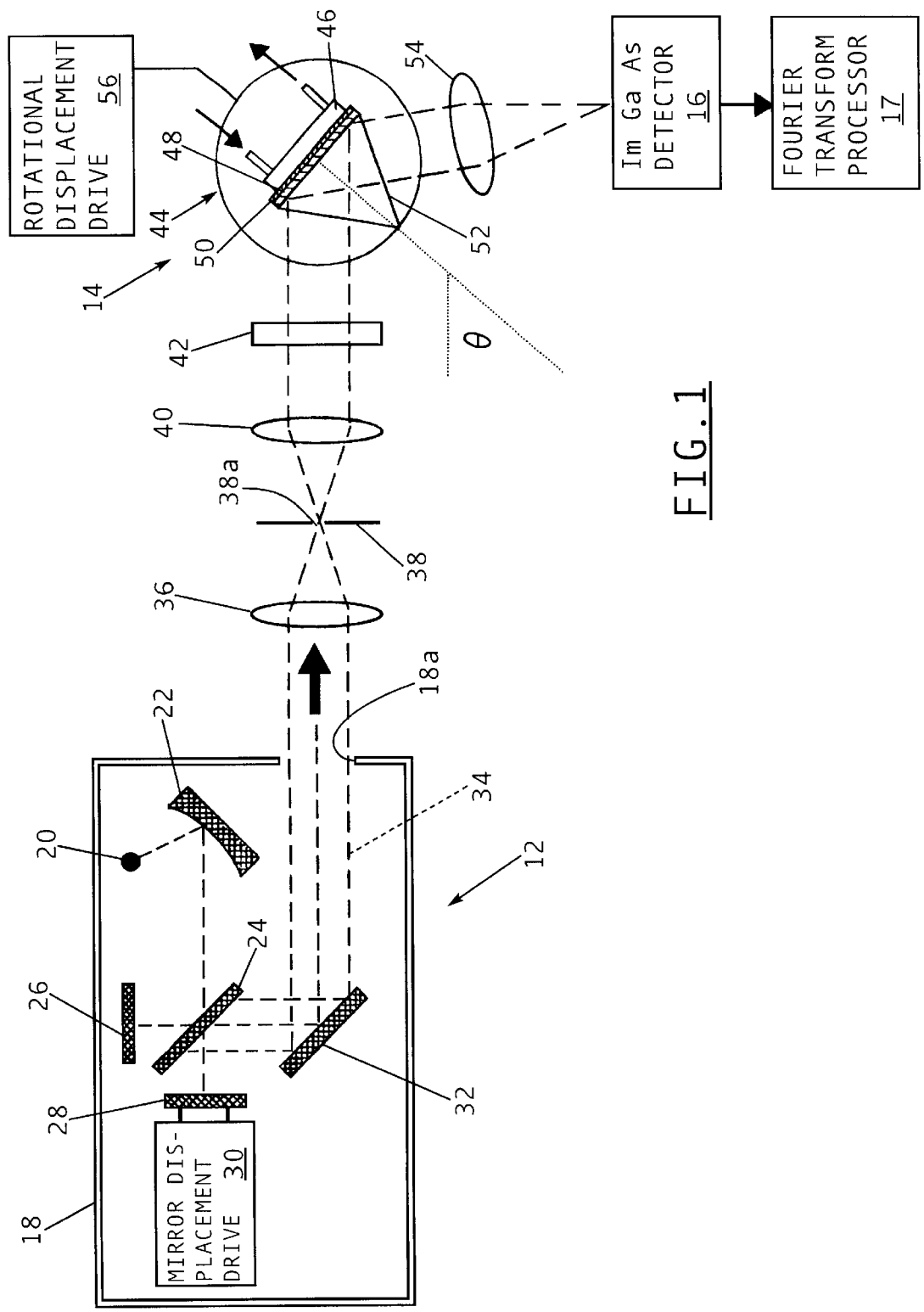
FIG. 1 is a simplified combined block and schematic diagram of a Fourier Transform surface plasmon resonance (FT-SPR) adsorption sensor instrument in accordance with the present invention.

Referring to FIG. 1, there is shown in simplified schematic and block diagram form a Fourier Transform surface plasmon resonance (FT-SPR) adsorption sensor apparatus 10 in accordance with the principles of the present invention.

The FT-SPR apparatus 10 includes a Michelson interferometer 12, an SPR instrument 14, suitable optics including various lenses and a polarizer 42, and a detector 16.

Interferometer 12 is conventional in design and operation and may include a generally closed housing 18 having an exit beam port 18a therein. Disposed within housing 18 is a broadband light source 20 for emitting radiation which is directed onto a source optics mirror 22 in the form of a collimating mirror. A collimated beam provided by the source optics mirror 22 is directed onto a beamsplitter 24. Beamsplitter 24 reflects a portion of the collimated beam onto a fixed mirror 26 and allows the remaining portion of the beam to be incident upon a moving mirror 28. Moving mirror 28 is coupled to and displaced by a mirror displacement drive 30 for displacing the moving mirror along the axis of the collimated beam provided by the source optics mirror 22. Beamsplitter 24 thus divides the incident beam into two paths, one on the fixed mirror 26 and the other on the movable mirror 28, and then recombines the two beams after a path difference has been introduced by the moving mirror. A condition is thus created under which interference between the beams can occur giving rise to intensity variations of the beam emerging from the interferometer 12 which can be measured as a function of path difference by a detector. Because of the effect of this interference, the intensity of the beam passing to a detector depends on the difference in the path length of the beams in the two arms of the interferometer, i.e., the fixed mirror and moving mirror path lengths. It is the variation in the length of the movable reflector beam path which provides the intensity modulation of the output of the interferometer. The collimated beam 34 produced by the interferometer 12 is intensity modulated by displacing the moving mirror 28 in a reciprocating manner. The beams from the fixed mirror 26 and the moving mirror 28 are combined and directed onto a beam steering mirror 32 which reflects the combined beam through the small exit beam port 18a in the interferometer's housing 18. While the present invention is described herein as incorporating a Michelson interferometer, virtually any type of interferometer which employs intensity modulation of the output beam may be used.

The collimated output beam 34 from interferometer 12 is directed to the SPR instrument 14. The SPR instrument 14 includes a beam collimator comprised of the combination of a first focussing lens 36, a second collimating lens 40, and a pinhole 38a in a plane or partition 38 which is disposed between the first and second lenses. The combination of the first and second lenses 36,40 and the light passing pinhole 38a improves the collimation of the output beam from the interferometer 12. The collimated beam is then passed through a polarizer 42 for providing a p-polarized beam. The p-polarized light beam can be coupled into the plasmon mode because its electric field vector oscillates normal to the plane containing the metal film described hereafter. The polarized light beam is directed to a sample cell 44 containing the sample in the form of a thin layer 48 to be analyzed. The sample cell 44 further includes a thin metal film 50 on a first surface of which is disposed the thin layer sample 48. In contact with the surface of the thin metal film 50 is a flow cell 46 for delivering the sample 48 for deposit on the thin metal film in the form of a thin layer. Disposed on a second, opposed surface of the thin metal film 50 is a triangular prism 52 through which the polarized light beam is directed onto the thin metal film. The polarized light beam undergoes internal reflection in the triangular prism 52 and is reflected off of the thin metal film 50 and out of the sample cell 44. The thin metal film 50 is preferably comprised of gold, silver or copper, with gold the prime choice for SPR measurements because of its resistance to oxidation. The thin metal film on which the receptor surface or sample is deposited may be comprised of various metals, with the main criteria of the thin metal film being that it have a negative real dielectric component. The triangular prism 52 is typically comprised of glass, although various other materials having suitable optical properties for internally reflecting the polarized incident beam and transmitting the reflected SPR beam may be used equally as well.

The reflected SPR beam is provided to a third lens 54 for focussing the beam onto a detector 16 preferably having high sensitivity in the appropriate spectral region. The detector 16 may be comprised of Si, Ge, InAs or InGaAs. The detector output signal is commonly referred to as an interferogram and is processed using standard Fourier Transform techniques using a Fourier Transform processor 17. The sample cell 44 may be coupled to a rotational displacement drive 56 for changing the angle of incidence of the polarized light beam on the thin layer sample 48 and measuring an SPR reflection minimum in analyzing the thin layer sample 48 disposed on the thin metal film 50.

Figure 2:
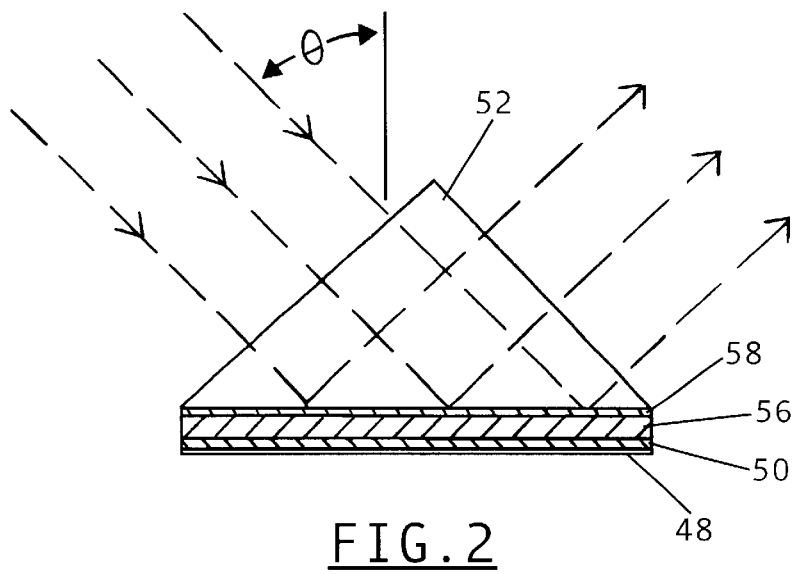
FIG. 2 is a simplified schematic diagram of one embodiment of a prism-sample assembly for use in the apparatus of FIG. 1.

Referring to FIG. 2, there is shown a simplified sectional view of additional details of the optical arrangement in the sample cell described above. As described above, the thin layer sample 48 is disposed on a first surface of the thin metal film 50. Disposed on a second, opposed surface of the thin metal film 50 is a glass cover sheet 56. The glass cover sheet 56 is brought into optical contact with the triangular glass prism 52 by means of a thin layer of index-matching fluid 58 such as ethylene glycol. As shown in FIG. 2, the angle of incidence of the incoming beam is θ and the incident and reflected beams are highly collimated.

Figure 3:
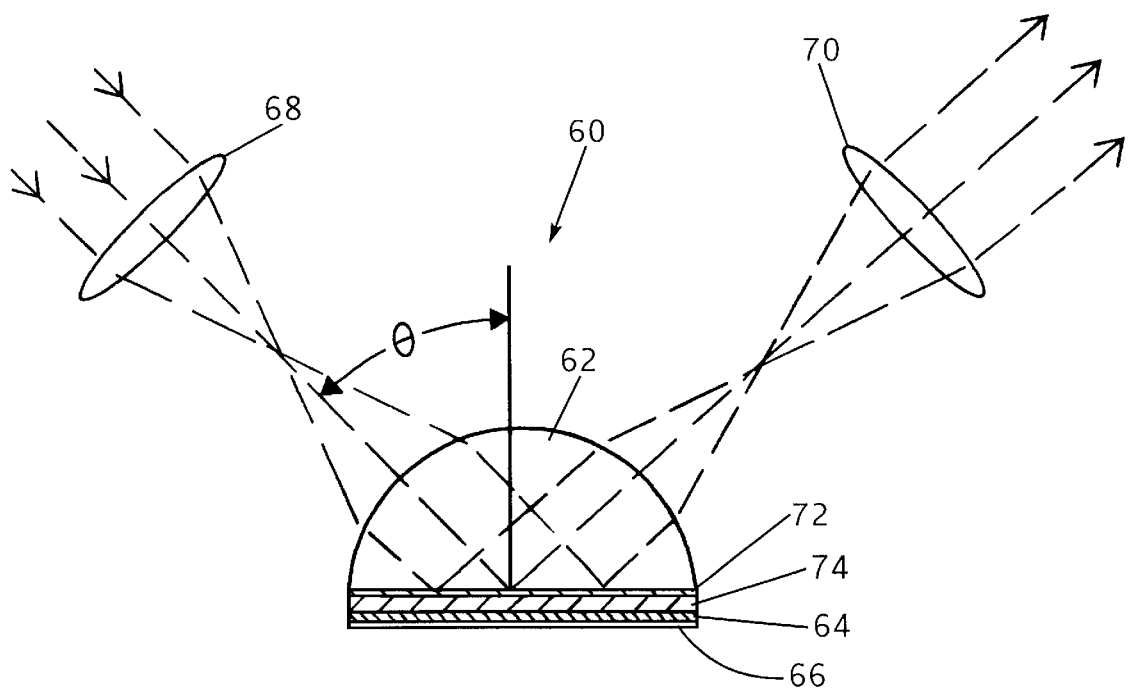
FIG. 3 is a simplified schematic diagram of another embodiment of a prism-sample assembly for use in the apparatus of FIG. 1.

Referring to FIG. 3, there is shown a simplified schematic diagram of another sample cell 60. As in the previous embodiment, a thin layer sample 66 is disposed on a first surface of a thin metal film 64. Disposed on a second, opposed surface of the thin metal film 64 is a glass cover sheet 74 and a contact fluid 72. A hemispherical glass prism 62 is disposed in contact with the contact fluid 72 on the surface of the glass cover sheet 74. The polarized beam incident on the sample cell 60 is directed through a first lens and onto the hemispherical prism 62. The beam is internally reflected by the prism 62 onto the thin metal film 64. The reflected beam is then directed through a second lens 70 to a detector which is not shown in the figure for simplicity. As shown in the figure, the first focusing lens 68 and the second collimating lens respectively compensate for the collimating and focusing effects of the hemispherical prism 62.

Figure 4:
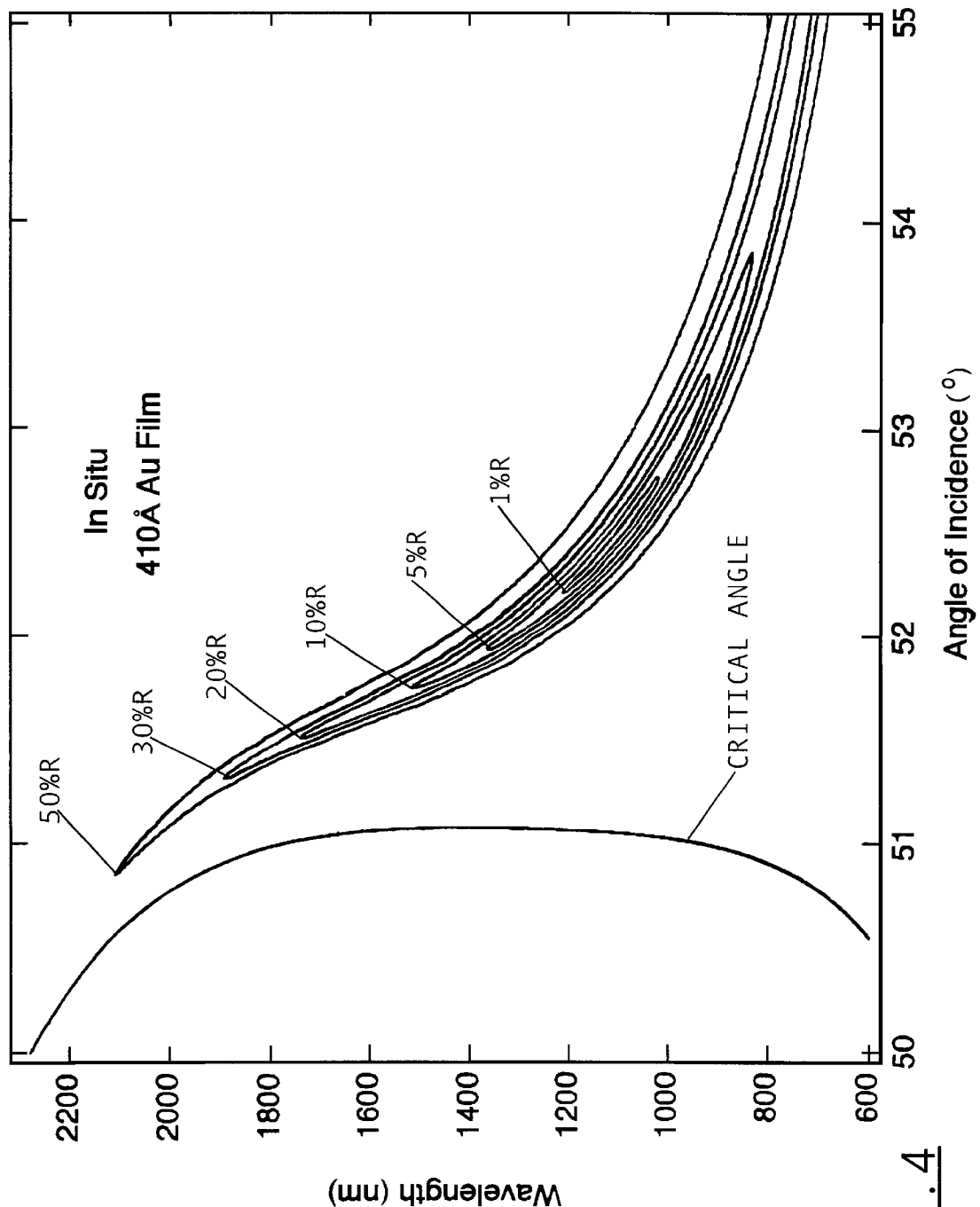
FIG. 4 is a graphic representation of the variation of reflectivity based upon Fresnel reflectivity calculations from a 41 nm gold film as a function of the wavelength and incident angle of a light beam with a glass prism/gold film/water interface in the sample cell.

Referring to FIG. 4, there is shown a reflectivity contour plot as a function of wavelength and incident angle of wideband light on a 41 nm gold film in an in situ configuration. In situ refers to an SPR sample cell having a glass prism/gold film/water configuration. The reflectivity contour plot shown in FIG. 4 is based upon Fresnel reflectivity calculations. Shown in FIG. 4 is the variation of reflectivity (R) as a function of wavelength of the incident light in nm and the angle of incidence of the incident light beam. As a contour plot, the graphic representation of FIG. 4 is three dimensional, with reflectivity extending outward from the plane of the figure. The line extending from the top to the bottom and positioned on the lefthand portion of the graph represents the wavelength dependence of the critical angle for the glass prism/gold film/water configuration under consideration. The smallest, inner, generally elliptical curve in the center of the graph represents the region where only 1% of the incident light is reflected. For optimum measurement sensitivity, the reflectivity should be minimized. Thus, the curve exhibiting 1% R represents the optimum incident light wavelength/SPR angle of incidence for this particular configuration, i.e., a 41 nm gold film in an in situ configuration. Also shown are reflectivity curves for 5% R, 10% R, 20% R, 30% R and 50% R.

Figure 5:
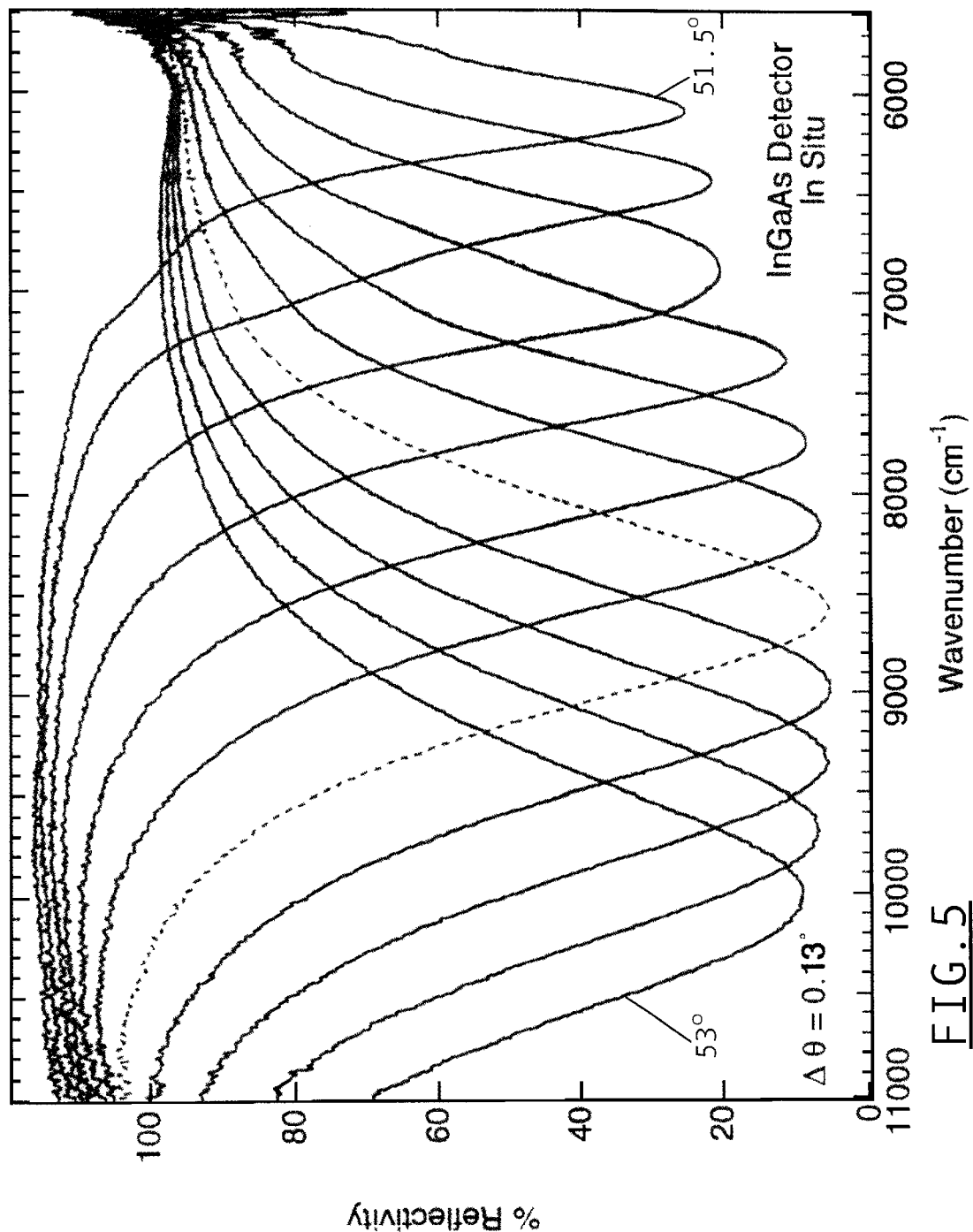
FIG. 5 shows the variation in percent reflectivity with the frequency of the incident radiation for various angles as measured by the FT-SPR adsorption sensor instrument of the present invention as generally shown in FIG. 1.

Referring to FIG. 5, there is shown the measured variation in percent reflectivity with wavenumber of the incident light for the in situ configuration described above with respect to FIG. 4. In FIG. 5, each curve represents a vertical line, or slice, through the contour plot of FIG. 4 for a range of angles of incidence. The lefthand curve represents FT-SPR measurements in the in situ mode previously described for an angle of incidence of 53°. Each curve in proceeding from left to right represents a decrease in the angle of incidence of 0.13°, with the last curve on the right representing the % reflectivity for an angle of incidence of approximately 51.5%. The wavenumber of the incident light ranges from 5600–11000 cm$^{-1}$. From FIG. 5, it can be seen that the reflectivity minima shift with decreasing wavenumber (or frequency), or increase with wavelength, as the angle of incidence decreases. The measured data shown in FIG. 5 is validated by the Fresnel reflectivity calculations shown in FIG. 4 which also shows the reflectivity minima shifting to longer wavelengths with decreasing angle of incidence.

Figure 6:
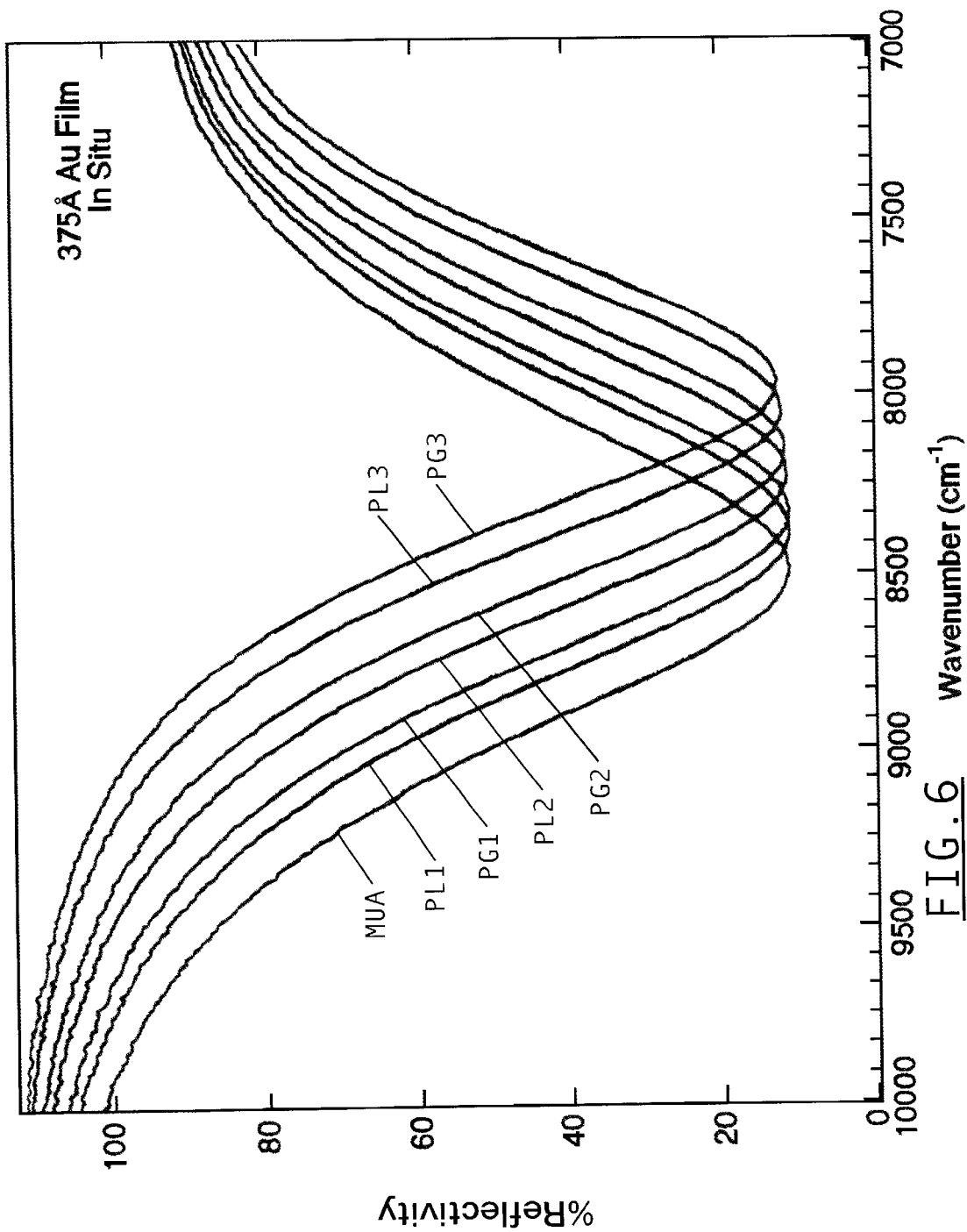
FIG. 6 shows graphically the variation in percent reflectivity with the frequency of the incident radiation for a thin surface layer disposed on a gold film, where the surface layer is provided with a range of thicknesses formed of various layers of proteins.

Referring to FIG. 6, there is shown a graphic representation of the variation in % reflectivity as a function of wavenumber of the incident light for a layered arrangement of proteins disposed on a 375 Å thick Au film for an in situ configuration. A monolayer of alkanethiol 11-mercaptoundecanoic acid (MUA) is first adsorbed on the surface of the Au film. The % reflectivity for the MUA monolayer on the Au film for a range of wavenumbers is shown as the left-most curve in FIG. 6. The wavelength shift was then measured for the sequential adsorption of alternating monolayers of poly-lysine (PL) and poly-glutamate (PG), where the first poly-lysine layer is labelled PL1, the second layer of poly-lysine is labelled PL2, etc. The sequential adsorption of the monolayers of PL and PG give rise to a wavelength shift. The PL layers have a thickness of 1.7 nm and give rise to a 100 cm$^{-1}$ shift in the frequency of the FT-SPR % reflectivity minimum. The PG layers have a thickness of 1.0 nm and give rise to an average shift of 60 cm$^{-1}$.

The data shown in FIG. 6 illustrates that the FT-SPR adsorption sensor instrument of the present invention provides a sensitive measurement of whether adsorption occurs and allows for the close monitoring of the thickness of a layer as it is absorbed onto the surface of the substrate.

Figure 7:
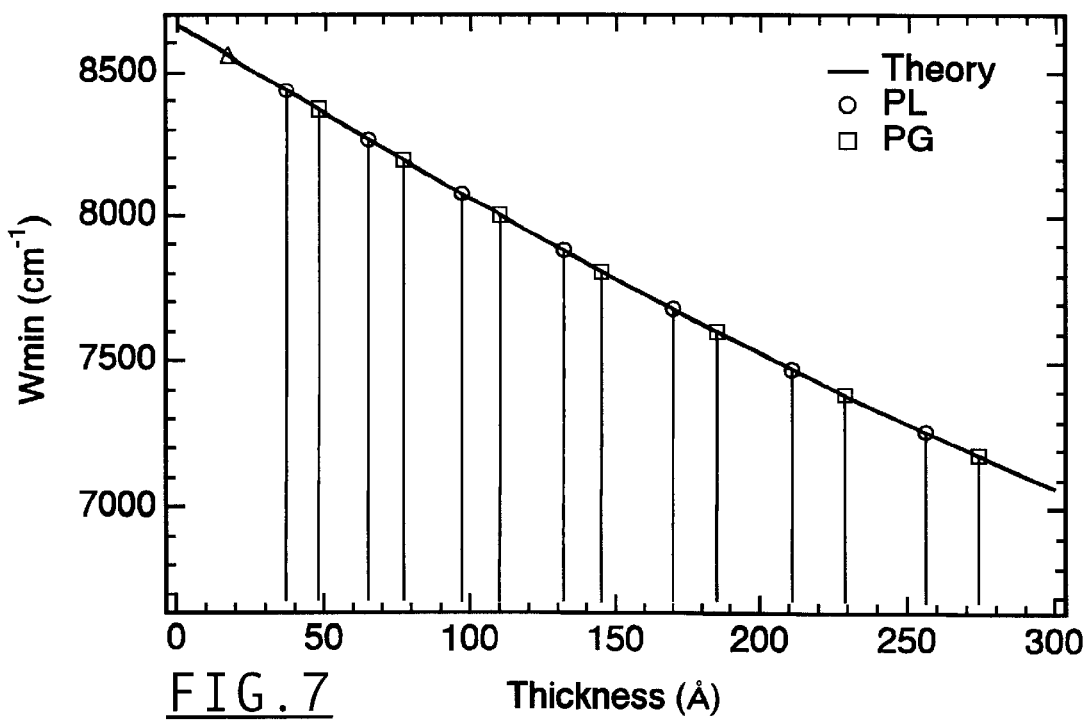
FIG. 7 is a graphic comparison of the measured and theoretical reflectance minima shift with variation in surface layer thickness for the alternating protein layer arrangement of FIG. 6.

FIG. 7 is a graphic comparison of the measured and theoretical reflectance minima shift with variation in surface layer thickness for the alternating protein layer arrangement of FIG. 6. The graphic comparison of FIG. 7 shows that the measured reflectance minima shift closely follows the theoretical calculated shifted values.

Figure 8:
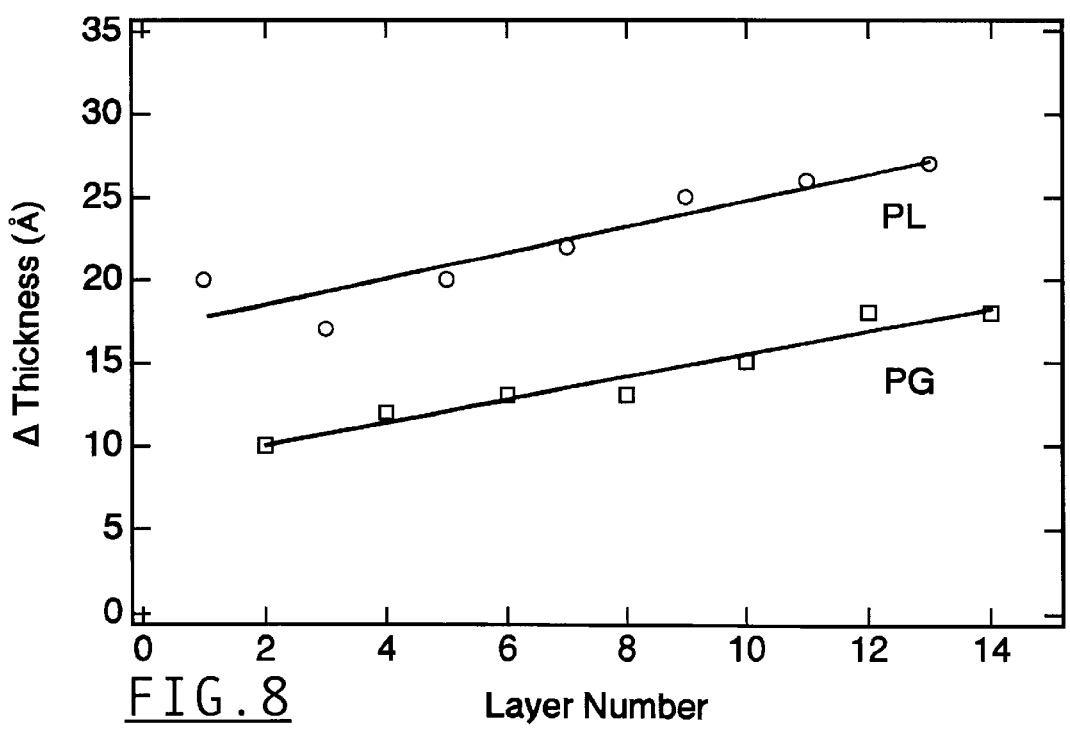
FIG. 8 is a graphic representation of the change in thickness for each layer of either polypeptide poly-L-lysine (PL) or poly-glutamate (PG).

FIG. 8 is a graphic representation of the change in thickness for each layer of either polypeptide poly-Lysine (PL) or poly-glutamate (PG). The data shown in FIG. 8 indicates an increase in thickness for each layer in proceeding away from the substrate on which the layers are deposited.

There has thus been shown apparatus for monitoring the adsorption of molecules onto thin metal films such as gold by surface plasma resonance (SPR) measurements which employs a Fourier Transform spectroscopy to measure the change of index of refraction at the sample-gold film interface. The FT-SPR apparatus measures reflectance spectra from a sample cell including a prism-metal film assembly at a well-defined angle of incidence. The FT-SPR apparatus exploits the wavelength sensitivity of the resonance by keeping the angle of incidence fixed, and measuring the SPR effect as a function of wavelength. The reflectance spectrum exhibits a pronounced minimum due to the SPR effect in the visible to near infrared (NIR) to infrared (IR) wavelengths. The position of the reflectance minimum can be varied by changing either the angle of incidence or the metal film thickness. The position of the reflectance minimum shifts in wavelength upon the adsorption of sample molecules onto the metal surface due to the change of index of refraction at the sample-gold film interface. The FT-SPR apparatus can be used to study the adsorption onto a chemically modified metallic surface from the gas phase as well as from liquid solutions. In particular, the adsorption of biological molecules such as DNA, proteins, antibodies, and enzymes from aqueous solutions can be monitored in situ with the inventive FT-SPR apparatus. The advantages of the inventive FT-SPR apparatus include excellent wavelength stability and measurement reproducibilty, fast data acquisition rates and high signal-to-noise outputs, as well as a broadened spectral range and high ordinate precision over which SPR measurements can be made.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawing is offered by way of illustration only and not as a limitation. The actual scope of the invention is intended to be defined in the following claims when viewed in their proper perspective based on the prior art.

We claim:

1. Apparatus for measuring the adsorption of molecules onto a thin metal film, said apparatus comprising:

means for providing an interferometrically modulated broadband beam of electromagnetic radiation;

beam processing means for collimating and polarizing said beam of electromagnetic radiation;

a prism transparent to electromagnetic radiation and having first and second surfaces, wherein a first surface of the thin metal film is in intimate contact with the second surface of said prism, and wherein said beam of electromagnetic radiation is incident upon the first surface of said prism and is internally reflected by said prism at the second surface;

means for introducing the molecules to a second, opposed surface of the thin metal film so as to form a molecular attachment thereon, wherein said beam of electromagnetic radiation gives rise to surface plasmon resonance at the metal film/molecular attachment interface having characteristics dependent upon the adsorption of molecules on the thin metal film; and detector means responsive to the internally reflected beam of electromagnetic radiation for providing an output signal representing the surface plasmon resonance on the thin metal film, wherein said output signal is processed using Fourier transform techniques.

2. The apparatus of claim 1 wherein said means for providing a interferometrically modulated broadband beam of electromagnetic radiation includes a Michelson interferometer.

3. The apparatus of claim 1 wherein said beam processing means includes a collimator including a first focusing lens, a second collimating lens, and means for defining a small aperture disposed intermediate said first focusing and second collimating lenses, and wherein said beam of electromagnetic radiation is directed through said small aperture.

4. The apparatus of claim 3 wherein said first focusing lens focuses said beam of electromagnetic radiation on said small aperture.

5. The apparatus of claim 4 wherein said beam processing means further includes a p-polarizer.

6. The apparatus of claim 1 further comprising drive means coupled to said thin metal film and prism for rotationally displacing said thin metal film and prism and changing an angle of incidence of said beam of electromagnetic radiation on said thin metal film.

7. The apparatus of claim 1 wherein said prism is triangular, with the thin metal film disposed on a first surface of said prism and wherein said beam of electromagnetic radiation is incident upon and emerges from second and third surfaces, respectively, of said prism.

8. The apparatus of claim 1 wherein said prism is hemispherical having a first curvilinear surface and a second flat surface, and wherein said beam of electromagnetic radiation is incident upon and emerges from the first curvilinear surface of said prism and the thin metal film is disposed on the second flat surface of said prism.

9. The apparatus of claim 8 further comprising optical means for compensating for collimating and focusing effects of said hemispherical prism on said beam of electromagnetic radiation.

10. The apparatus of claim 9 wherein said optical means includes a first focusing lens for directing said beam of electromagnetic radiation onto said hemispherical prism and a second collimating lens for directing said beam emerging from said hemispherical prism to said detection means.

11. The apparatus of claim 10 further comprising a third lens for focusing the beam onto said detector means.

12. The apparatus of claim 1 wherein said detector means is comprised of Si, Ge, InAs or InGaAs.

13. Apparatus for measuring the activity of biological molecules on a thin metal film, said apparatus comprising:

beam generating means for providing an inteferometrically modulated broadband beam of electromagnetic radiation;

beam processing means for collimating and polarizing said beam of electromagnetic radiation in a plane of incidence of said beam;

optical means transparent to electromagnetic radiation and including first and second surfaces, wherein said optical means receives the collimated and polarized beam of electromagnetic radiation from said beam processing means at its first surface and internally reflects said beam of electromagnetic radiation at its second surface, and wherein a first surface of the thin metal film is in intimate contact with the second surface of said optical means;

means for introducing the biological molecules to a second, opposed surface of the thin metal film so as to form a molecular attachment thereon, wherein said beam of electromagnetic radiation gives rise to surface plasmon resonance at the metal film/molecular attachment interface having characteristics dependent upon the adsorption of biological molecules on the thin metal film; and detector means responsive to the internally reflected beam of electromagnetic radiation for providing an output signal representing the surface plasmon resonance on the thin metal film, wherein said output signal is processed using Fourier transform techniques.

* * * * *